United States Patent [19]

Larson et al.

[11] Patent Number: 5,445,154

[45] Date of Patent: Aug. 29, 1995

[54] ULTRASONIC PROBE ASSEMBLY WITH LINEAR ACTUATOR

[75] Inventors: Paul Larson, Boalsburg; Rickey L. Wagner, Reedsville, both of Pa.

[73] Assignee: Interspec, Inc., Ambler, Pa.

[21] Appl. No.: 112,564

[22] Filed: Aug. 26, 1993

[51] Int. Cl.⁶ .................................. A61B 8/12
[52] U.S. Cl. .................. 128/660.1; 128/662.06
[58] Field of Search .................. 73/620, 633; 128/660.07, 660.09, 660.10, 662.05, 662.06

[56] References Cited

U.S. PATENT DOCUMENTS

| | | | |
|---|---|---|---|
| 4,271,706 | 6/1981 | Ledley | 73/614 |
| 4,282,879 | 8/1981 | Kunii et al. | 73/621 |
| 4,434,659 | 3/1984 | Kurtz et al. | 73/633 |
| 4,455,872 | 6/1984 | Kossoff et al. | 73/618 |
| 4,807,634 | 2/1989 | Enjoji et al. | 128/660.01 |
| 4,967,752 | 11/1990 | Blumenthal et al. | 128/660.1 |
| 5,191,890 | 3/1993 | Hileman | 128/662.06 |
| 5,215,092 | 6/1993 | Wray | 128/662.06 |

*Primary Examiner*—F. Jaworski
*Attorney, Agent, or Firm*—W. Brinton Yorks, Jr.

[57] ABSTRACT

An ultrasonic probe assembly in which the disposition of the scan plane of an ultrasonic transducer is achieved using a linear actuator. The scan plane is selected by operation of a remote control unit which, through cables, controls the linear actuators and associated gears and, thus, the rotation of the ultrasonic transducer.

20 Claims, 3 Drawing Sheets

ULTRASONIC PROBE ASSEMBLY WITH LINEAR ACTUATOR

FIELD OF THE INVENTION

The present invention relates, in general, to ultrasonic imaging and, in particular, to a probe in which the scan plane of an ultrasonic transducer unit can be changed with a linear actuator system, so that a body organ which is being imaged can be viewed in different ways (i.e. in longitudinal and transverse planes or any plane in between).

BACKGROUND OF THE INVENTION

Many different ultrasonic multi-plane probes, arranged for positioning within the body, have been suggested or put into actual use in the past. Certain of these prior art ultrasonic multi-plane probes are arranged with the ultrasonic transducer array located within a cylindrical housing. To rotate the ultrasonic transducer array of these probes, the ultrasonic transducer array is mounted upon a pulley or shaft. The pulley is directly connected to a cable which rotates the pulley and, in turn, the ultrasonic transducer array.

Some probes contain a transducer array inside of a cavity within a cylindrical housing. It is common practice in the design of these probes to fill the cavity in which the ultrasonic transducer array unit is located with a fluid or viscous acoustic coupling material, such as a grease, and to cover the cavity with a membrane or lens element. The viscous acoustic coupling material is provided in such probes to establish the acoustic coupling from the array into the membrane. The presence of the fluid in the cavity in the probe housing is the source of potential damage to the ultrasonic transducer array. The viscous coupling material is an extra element in the acoustic path and can cause attenuation and distortion of the desired signals.

Other multi-plane probes locate the ultrasonic transducer external to the base unit. Probes of this type provide direct contact between the ultrasonic transducer array and body tissue, such as the lining of the esophagus. Direct contact reduces or eliminates possible signal attenuation and distortion.

A problem with multi-plane probes of the prior art is the lack of control for accurate rotation of the transducer array to desired preset positions in order to rotate to, and maintain the transducer array at, a desired position.

A further problem with prior art ultrasonic multi-plane probes is that when examining a patient's body, it is necessary to reposition the probe in the esophagus, to get the best alignment of the transducer with the organ being examined. In doing so, it is necessary to flex the probe unit cable which, in turn, causes the internal rotation control cables to move. This results in the transducer array rotating slightly, changing its alignment.

SUMMARY OF THE INVENTION

An ultrasonic probe assembly, constructed in accordance with the present invention, includes a base unit and ultrasonic transducer means for scanning in a scan plane. The ultrasonic transducer means and connected ultrasonic transducer mount are pivotally movable relative to the base unit through a positioning angle which extends in a plane perpendicular to the scan plane, thereby changing the disposition of the scan plane. The pivotal movement is achieved by a drive means for rotating the transducer mount through a plurality of angular positions about a single point. A control means indexedly controls the drive means responsive to a remote control unit.

In one exemplary embodiment, the drive means includes a drive gear attached to a cup-shaped and circular plate which in turn is connected to the transducer mount. A drive train is linked to the drive gear. The drive train is driven by a ratchet gear connected to a pair of ratchet wheels (one for each direction) which are controlled by two spring loaded, linear sliding pawls, respectively. A pair of solenoids steps the pawls for desired motion of the array by pulling on control cables attached to the pawls.

In another exemplary embodiment, the ultrasonic transducer means are mounted on a transducer mount which in turn is mounted external to the base unit so that the emitting surface of the ultrasonic transducer means at which an ultrasound beam is formed is external to the base unit.

In another exemplary embodiment constructed in accordance with the present invention, sealing means are included to prevent external fluids from entering the base unit.

In another exemplary embodiment constructed in accordance with the present invention, the ultrasonic transducer means include an ultrasonic array and an array mount upon which the ultrasonic array is mounted. It will be understood, however, that the underlying concept of the present invention can be applied to probes having transducers which are scanned mechanically.

BRIEF DESCRIPTION OF THE DRAWINGS

The invention will now be described by way of non-limiting examples, with reference to the drawings in which.

DETAILED DESCRIPTION OF THE INVENTION

Figure 1:
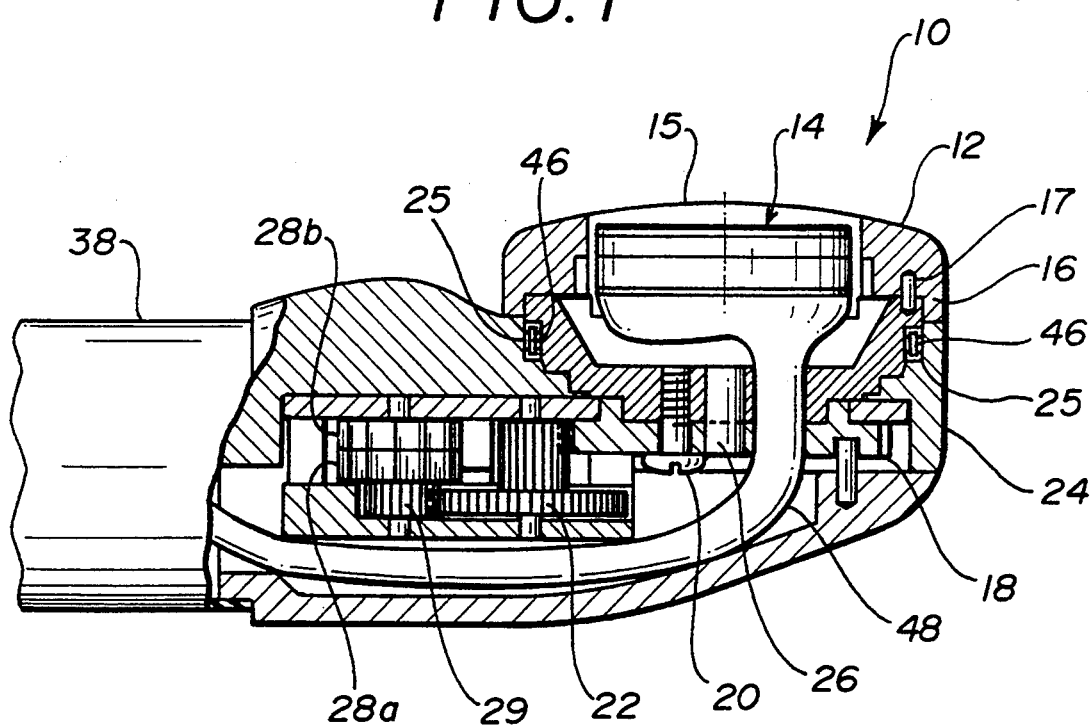
FIG. 1 is a vertical cross sectional view of the probe portion of an exemplary embodiment of an ultrasonic probe assembly constructed in accordance with the present invention.
Figure 2:
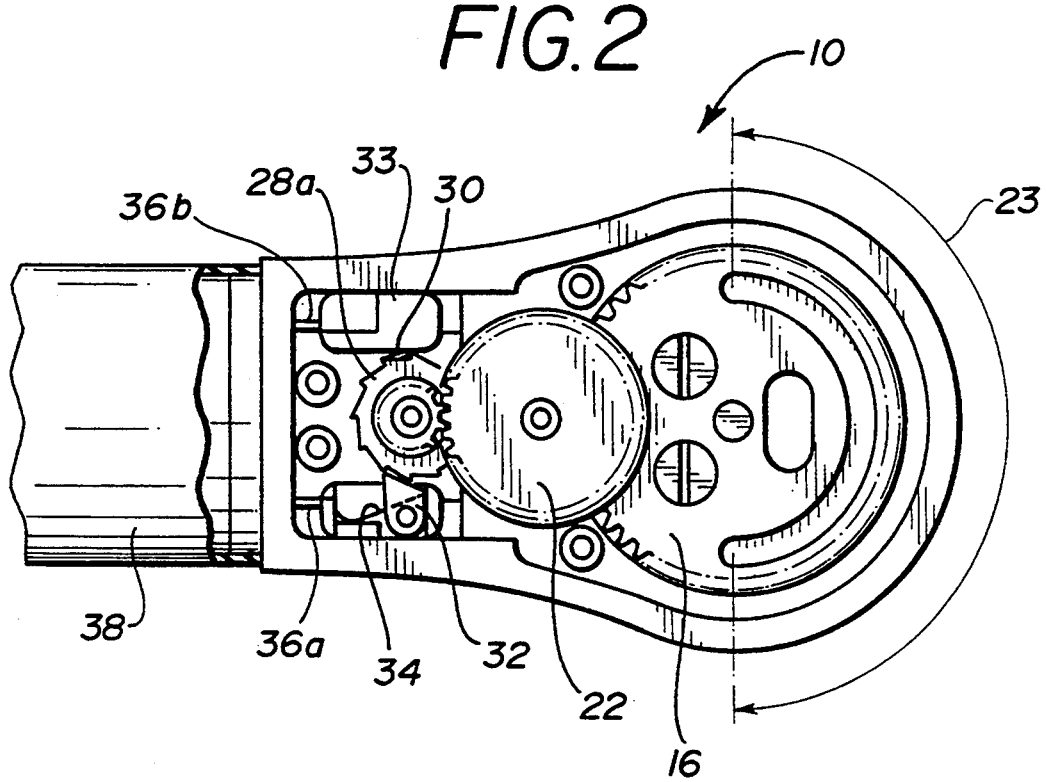
FIG. 2 is a horizontal cross sectional view of the probe portion of FIG. 1.

Referring to FIGS. 1 and 2, an ultrasonic probe assembly 10, constructed in accordance with the present invention, includes a base unit 24 and a transducer mount 12 upon which is mounted an ultrasonic transducer array 14. Ultrasonic transducer array 14 can be of conventional construction and operation and is preferably a multi-element phased array ultrasonic transducer. The array may be a linear array or a curved linear array. This multi-element phased array forms an ultrasonic beam emitted from surface 15 of ultrasonic transducer array 14 and is scanned in a plane projecting into the paper for the view shown in FIG. 2. Those skilled in the art will understand that ultrasonic transducer array 14 can be interchanged with other forms of transducer assemblies, such as mechanically scanned transducers with appropriate scanning mechanisms.

Transducer mount 12 is mounted to a member 16, which in this exemplary embodiment is cup-shaped and circular. Other shapes for member 16 are fully within the scope of this disclosure. Transducer mount 12 and, cupped member 16 are fastened together for rotation by a pin 17 and form an array mount by which ultrasonic transducer array 14 is mounted to base unit 24.

Cupped member 16 is, in turn, secured to a drive gear 18 via a fastener 20. Fastener 20 is shown as a screw although other fastening means may be used. Drive gear 18 is, in turn, engaged with a gear train 22. Gear train 22 reduces the rotation step motion of the ultrasonic transducer array as well as the amount of force necessary to rotate the ultrasonic transducer array 14 and its attached components. Gear train 22 is engaged with a ratchet wheel gear 29. For the embodiment of the invention illustrated in FIGS. 1 and 2, drive gear 18, gear train 29 and ratchet wheel gear 29 form drive means by which the array mount 12 and transducer array 14 are rotated through a plurality of angular positions about the axis of a pivot pin 26 by which cupped member 16 is positioned in base unit 24. Accordingly, ultrasonic transducer array 14 is pivotally moveable relative to base unit 24 through a positioning angle which extends in a plane perpendicular to the scan plane of ultrasonic transducer array 14, namely in a plane perpendicular to the paper for the section shown in FIG. 1 and parallel to the paper for the section shown in FIG. 2. The plane of the positioning angle is perpendicular to the pivot axis of pivot pin 26. In this exemplary embodiment, the range of rotation of the scan plane of ultrasonic transducer array 14 is approximately 180° as indicated by directional line 23 in FIG. 2. Because the scan plane is symmetrical about the axis of rotation, this range of motion provides an effective 360° of total scanning range. In order to insure that a full 360° of scanning range is achieved, the range of rotation may be engineered to be slightly more than 180°.

Ultrasonic transducer array 14, transducer mount 12 and cupped member 16 are three elements which are mounted external to base unit 24, in an exemplary embodiment of the present invention, to provide the benefits which result from external mounting. Specifically, external mounting allows for a large array to be used. Further, external mounting allows the array to be in direct contact with a body part to minimize signal loss and distortion; other benefits will be understood by those skilled in the art. The present invention also includes, however, multi-plane probes which have an ultrasonic transducer array mounted within a base unit.

The present invention further includes control means for indexedly controlling the drive means. For the embodiment of the invention being described, the control means comprises a pair of ratchet wheels 28a and 28b, a pair of linear sliding pawls 32 (only one is illustrated), a pair of springs 34 (only one is illustrated) and a pair of control cables 36a and 36b.

Ratchet wheels 28a and 28b have separate sets of ratchet teeth 30, with each set of ratchet teeth 30 disposed in a direction opposite that of the other set of ratchet teeth 30. Ratchet wheel 28a and ratchet wheel 28b are stacked, one on top of the other, and turn as a single integrated piece. Attached to ratchet wheel 28a and ratchet wheel 28b is ratchet wheel gear 29. Ratchet wheel 28a, ratchet wheel 28b and ratchet wheel gear 29 may be a single piece.

Ratchet wheels 28a and 28b are indexed by separate linear sliding pawls 32, which individually engage ratchet teeth 30 of the respective ratchet wheels. In the sectional view of FIG. 2, only one linear sliding pawl 32 is shown—the linear sliding pawl 32 which engages ratchet wheel 28a. The other linear sliding pawl, which engages ratchet wheel 28b, operates identical to the linear sliding pawl 32 shown, except that it operates for rotation of ratchet wheel 28b in the opposite direction. The other linear sliding pawl, which engages ratchet wheel 28b, is positioned for engagement of teeth 30 of ratchet wheel 28b. In the exemplary embodiment shown in FIG. 2, the other linear sliding pawl and its supporting components are located in the area labeled 33 and aligned to engage ratchet wheel 28b which is positioned above ratchet wheel 28a (as shown in FIG. 1). The remaining description will apply equally to the other linear sliding pawl 32 and supporting components which are not shown in the sectional view of FIG. 2.

One of the springs 34 allows its associated linear sliding pawl 32 to lift over ratchet teeth 30 and disengage from an individual ratchet teeth 30 of the associated ratchet wheel 28a (or 28b) on a return stroke (i.e. in the direction opposite the direction of engagement of a particular linear sliding pawl) and then return to a position where linear sliding pawl 32 will engage ratchet teeth 30 on the next actuation.

Linear sliding pawls 32 are connected to associated control cables 36a and 36b. Control cables 36a and 36b are within tensioned spiral coiled wire jackets 37a and 37b. These control cables and their jackets pass through flexible protect shaft 38. It should be understood that cables 36a and 36b can take the form of rods, instead of cables.

Figure 3:
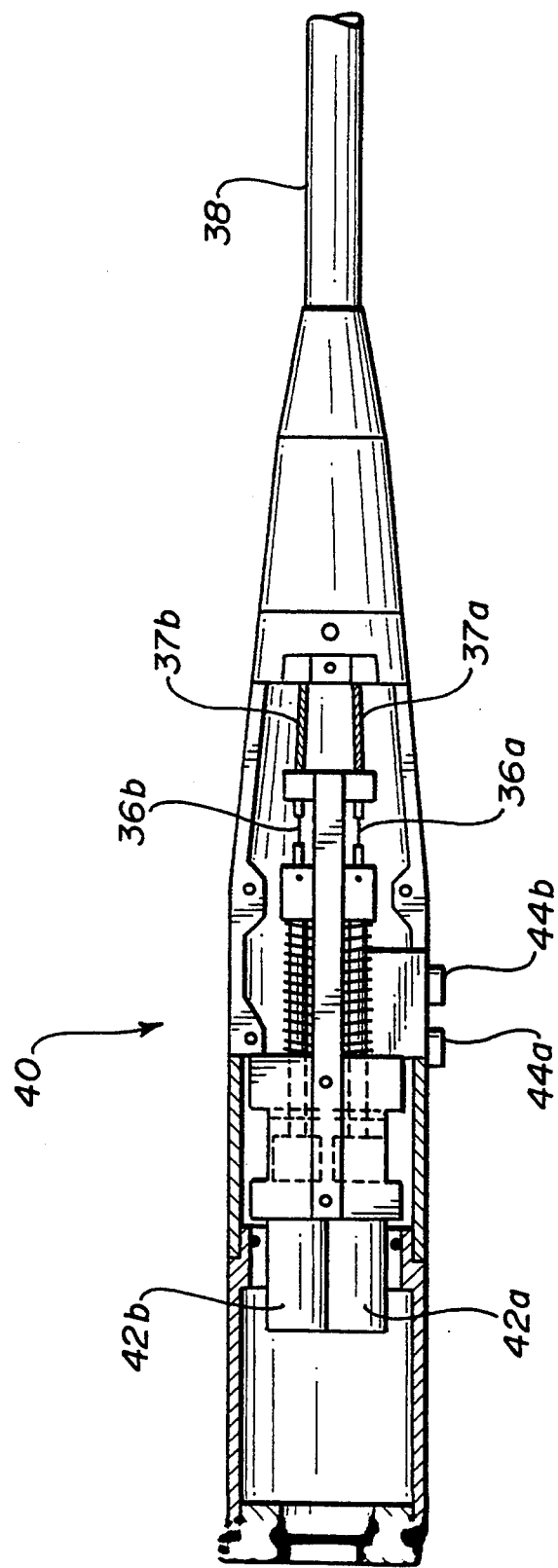
FIG. 3 is a horizontal cross sectional view of a remote control unit of an exemplary embodiment of a probe assembly constructed in accordance with the present invention.

Cables 36a and 36b are driven by spring loaded pull-type solenoids 42a and 42b, respectively, both of which are located in a remote control unit 40 shown in FIG. 3. Solenoids 42a and 42b are actuated by an electronic circuit which is controlled by an operator by means of electrical switches 44a and 44b, respectively, shown in FIGS. 3 and 4 and mounted on remote control unit 40. It should be understood that switches 44a and 44b can be replaced by other switching means which allows control of both solenoids. The controls may be mounted elsewhere on the probe or on the system or on a foot switch. In an exemplary embodiment, one solenoid produces clockwise rotation of the unit composed of ratchet wheels 28a and 28b and ratchet wheel gear 29, while the other solenoid produces counterclockwise rotation of this unit. It is fully within the spirit of this invention that a single bi-directional solenoid or other actuation means can be used.

Switches 44a and 44b may operate for individual incremental rotation (i.e. one increment of rotation for each switch contact) or continuous incremental rotation (i.e. a series of incremental rotations) if switch contact is maintained beyond a predetermined amount of time. This latter operation is similar to that of a cursor key in a word processor.

Springs 34 urge linear sliding pawls 32 toward their associated ratchet wheels 28a and 28b so that the linear sliding pawls are engaged into their associated ratchet wheels during the actuation stroke. To rotate ultrasonic transducer array 14 in a first direction, an operator closes switch 44a to actuate solenoid 42a. In the actuation stroke, solenoid 42a pulls cable 36a which, in turn, pulls linear sliding pawl 32, aided by the action of its associated spring 32, into engagement with teeth 30 of ratchet wheel 28a. Upon completion of the actuation stroke of solenoid 42a, ratchet wheel 28a advances one increment. On the return stroke, with solenoid 42a no longer actuated, the ramp shape of linear sliding pawl 32 lifts away from ratchet teeth 30 of ratchet wheel 28a and linear sliding pawl 32 returns to its initial position. The push of cable 36a is sufficient to overcome the spring force of spring 34 so that linear sliding pawl 32 can lift over teeth 30 on the return stroke. The return stroke moves the sliding pawl 32 beyond the ratchet teeth 30 so that it is free to be rotated by the opposite solenoid 42b. Friction inherent in the gear train (in addition to that provided by dynamic seal 46) holds the transducer array 14 stationary between actuations. The operation of the second linear sliding pawl is opposite to that just described when the direction of rotation of ultrasonic transducer array 14 is to be reversed.

As linear sliding pawl 32 engages and rotates ratchet wheel 28a, ratchet wheel gear 29 is also rotated. Ratchet wheel gear 29 rotates gear train 22 which, in turn, rotates drive gear 18. Drive gear 18 is connected to cupped member 16. Cupped member 16 is connected to transducer mount 12 on which is mounted ultrasonic transducer array 14. Thus, the linear motion of linear sliding pawl 32 is transformed into the rotational motion of ultrasonic transducer array 14.

Another way to view the operation of the linear sliding pawls 32 is to view them as moving from one clock position to another. During the actuation cycle, linear sliding pawl 32 moves from 2 o'clock to 4 o'clock and then returns to 2 o'clock on the return stroke. Ratchet wheel 28a is moved one increment from approximately 3 o'clock to 4 o'clock in cycle one. The other linear sliding pawl 32 is positioned away from ratchet wheel 28b at 10 o'clock during engagement of ratchet wheel 28a. For engagement in the other direction, the other linear sliding pawl would move from 10 o'clock to 8 o'clock, with the first linear sliding pawl positioned away from ratchet wheel 28a above 2 o'clock.

The starting reference angle of the array can be established by actuating one solenoid a sufficient number of times to rotate the array to a reference stop. An indication of subsequent position can be obtained by counting the number of steps taken from the initial reference position. In an additional embodiment, remote control unit 40 may have a digital counter to count the increments of rotation in either direction to provide visual feedback and confirmation of the position of ultrasonic transducer array 14.

A position sensor (not shown) may also be incorporated to measure the rotational position of ultrasonic transducer array 14 relative to base unit 24. The position sensor may take one of various forms, including a rotary potentiometer, a rotary inductive device or an optical encoder, which can indicate the scan plane of ultrasonic transducer array 14.

Also shown in FIG. 1 is a dynamic seal 46 mounted to the outside diameter surface of cupped member 16. The outside diameter surface of dynamic seal 46 contacts the inside diameter surface 25 of base unit 24. Dynamic seal 46 provides a means to prevent fluid (such as body fluid) from entering base unit 24. This prevention of entry of fluid occurs when cupped member 16 is either in a fixed position or rotating. Dynamic seal 46 is made of a low friction material such as polytetrafluoroethylene (PTFE), so as not to interfere or inhibit rotation of ultrasonic transducer array 14 during imaging. It is also possible to have a second low friction material attached to inside diameter 25 of base unit 24 which contacts dynamic seal 46.

Electrical signals are conducted to and from ultrasonic transducer array 14 by means of a bundle of wires 48 shown only in FIG. 1. Bundle of wires 48 is a bundle of coaxial cables in the exemplary embodiment of the present invention. Each coaxial cable in bundle 48 is connected to a single array element of ultrasonic transducer array 14. The individual wires in bundle of wire 48 are arranged to minimize bending stresses and rubbing forces as the scan plane disposition of ultrasonic transducer array 14 is being changed. Wire bending and flexing occurs mainly in the area under transducer array 14. To facilitate the connections to the individual array elements, a flex circuit can be used. Other connection means are possible. Bundle of wires 48 passes out of base unit 24 through flexible shaft 38, control unit 40 and a cable jacket 52 to suitable signal processing and imaging equipment 56 as shown in FIG. 4.

Figure 4:
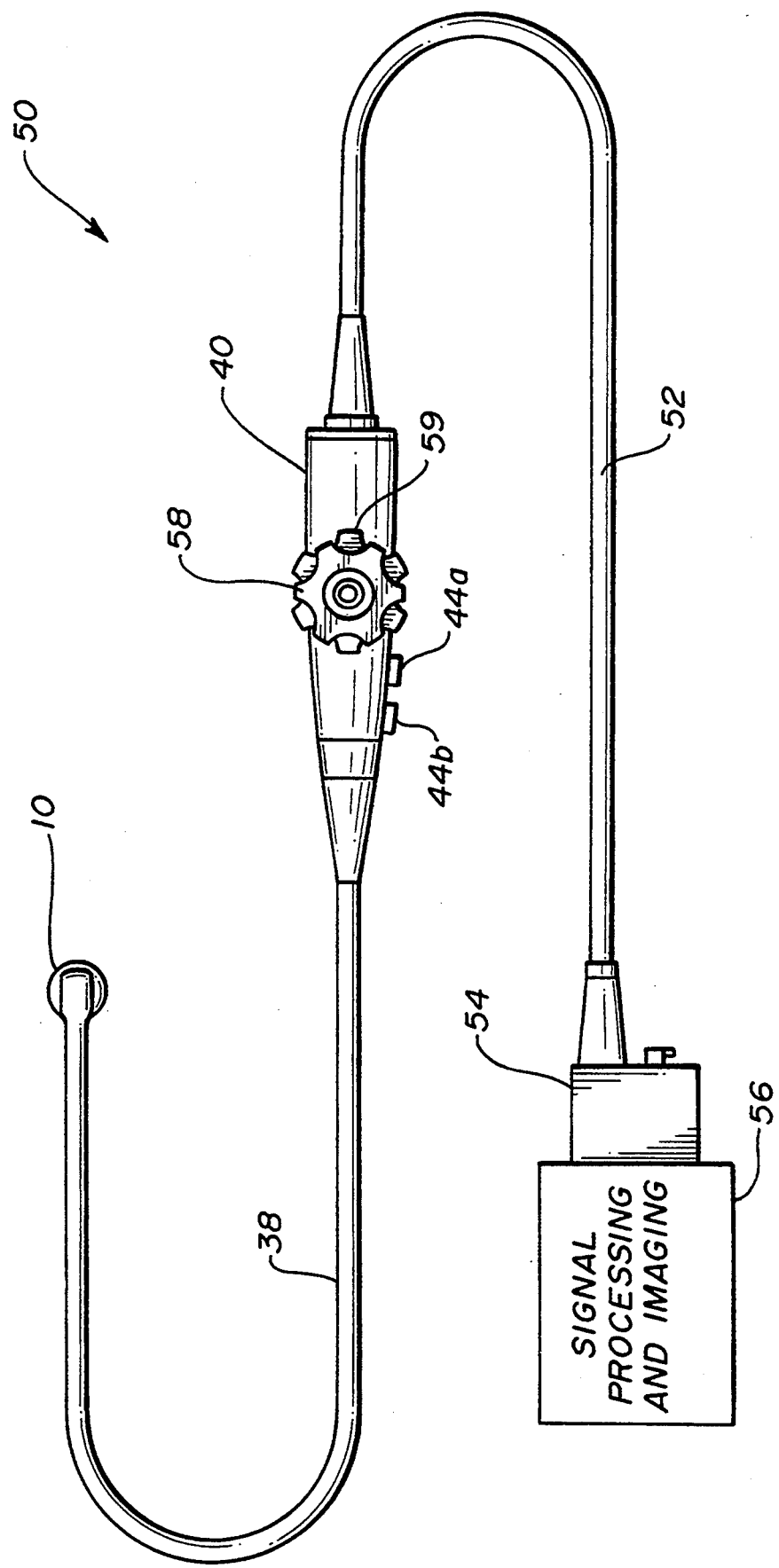
FIG. 4 is a plan view of a probe unit in which the probe portion of FIGS. 1 and 2 and the remote control unit of FIG. 3 can be incorporated in accordance with the present invention.

There is shown in FIG. 4 an ultrasonic probe assembly 10 of FIGS. 1 and 2, including remote control unit 40 of FIG. 3, which are incorporated into a probe unit 50. Base unit 24 (and, in turn, ultrasonic transducer array 14) are connected to remote control unit 40 via flexible shaft 38. Inside flexible shaft 38 are control cables 36a and 36b and bundle of wires 48 plus the rotation command signals from switches 44a and 44b.

Electrical signals are passed along bundle of wires 48 through remote control unit 40 and cable jacket 52 between the ultrasonic array and signal processing and imaging equipment 56.

A pair of knobs 58 and 59 on remote control unit 40 controls bending of the end of probe unit 50 upward, downward and sideways to permit the end of the probe unit to make turns as it is passed through the throat, for example, to enter the esophagus to image the heart. Knobs 58 and 59 also control the position of ultrasonic transducer array 14 against the esophagus for acoustic coupling and orientation of the transducer beam when probe unit 50 is used for imaging the heart.

The present invention can be used in many types of in-vitro multiplane scanning situations where the scan plane of an ultrasonic transducer array can be rotated. Some examples of areas where multiplane scanning can be used include: echo cardiography, radiology and laparoscopy.

The foregoing has set forth an exemplary and preferred embodiment of the present invention. It will be understood, however, that various other alternative embodiments will occur to those of ordinary skill in the art without departure from the spirit and scope of the present invention.

What is claimed:

1. An ultrasonic probe assembly comprising:
   a base unit;
   an ultrasonic transducer array unit mounted to said base unit and rotatable through a plurality of angular positions corresponding to different scan planes located about a single axis, said ultrasonic transducer array unit including:
   (a) an ultrasonic transducer array for scanning in a scan plane;
   (b) transducer mount upon which said ultrasonic transducer array is mounted;

a remote control unit for selecting an angular position of said ultrasonic transducer array;

drive means for rotating said ultrasonic transducer array through said plurality of angular positions about said single axis; and a linearly reciprocating device, coupled to said drive means, for indexedly controlling said drive means when moved linearly in a single direction in response to said remote control unit.

2. An ultrasonic probe assembly according to claim 1 wherein said drive means comprises:

a drive gear coupled to said transducer mount; and a ratchet wheel gear coupled between said drive gear and said linearly reciprocating device for rotating said drive gear in response to motion of said linearly reciprocating device.

3. An ultrasonic probe assembly according to claim 1 wherein said ultrasonic transducer array unit and said drive are located within the body of a patient while said ultrasonic transducer array unit scans in said scan plane;

said remote control unit is located outside said body; and said linearly reciprocating device extends into said body while said ultrasonic transducer array unit scans in said scan plane.

4. An ultrasonic probe assembly comprising:

a base unit;

an ultrasonic transducer array unit mounted to said base unit and rotatable through a plurality of angular positions about a single axis, said ultrasonic transducer array unit including:

(a) an ultrasonic transducer array for scanning in a scan plane;

(b) transducer mount upon which said ultrasonic transducer array is mounted;

a remote control unit for selecting an angular position of said ultrasonic transducer array;

drive means for rotating said ultrasonic transducer array to said plurality of angular positions about said single axis; and control means for indexedly controlling said drive means in response to said remote control unit;

wherein said drive means comprises:

a drive gear fastened to said transducer mount;

a gear train engaged with said drive gear for rotating said drive gear and said ultrasonic transducer array unit; and a ratchet wheel gear engaged with said gear train and said control means for rotating said gear train in response to said control means;

wherein said control means comprises:

a first indexed ratchet wheel having a first set of teeth oriented in a first tooth direction and a second indexed ratchet wheel having a second set of teeth oriented in a second tooth direction opposite to said first tooth direction;

a first linear sliding pawl adapted to engaged said first indexed ratchet wheel to rotate said first indexed ratchet wheel in a first ratchet wheel movement direction and a second linear sliding pawl adapted to engage said second indexed ratchet wheel to rotate said second indexed ratchet wheel in a second ratchet wheel movement direction opposite to said first ratchet wheel movement direction;

a first spring connected to said first linear sliding pawl and adapted to engage said first linear sliding pawl with said first ratchet wheel and a second spring connected to said second linear sliding pawl and adapted to engage said second linear sliding pawl with said second ratchet wheel; and a first control cable to move said first linear sliding pawl; and a second control cable to move said second linear sliding pawl.

5. An ultrasonic probe assembly according to claim 4, wherein said control means further comprises:

a first solenoid connected to said first control cable and adapted to pull said first control cable to engage said first linear sliding pawl with said first ratchet wheel on a first stroke of said first solenoid and to push said first control cable to disengage said first linear sliding pawl from said first ratchet wheel on a second stroke of said first solenoid; and a second solenoid connected to said second control cable and adapted to pull said second control cable to engage said second linear sliding pawl with said second ratchet wheel on a first stroke of said second solenoid and to push said second control cable to disengage said second linear sliding pawl from said second ratchet wheel on a second stroke of said second solenoid;

said first solenoid and said second solenoid adapted to engage only one of said respective first and second linear sliding pawls with said respective first and second ratchet wheels at a given time.

6. An ultrasonic probe assembly according to claim 5 wherein said remote control unit comprises first and second electrical switches for controlling said first and second solenoids, respectively.

7. An ultrasonic probe assembly according to claim 6 further comprising a bundle of wires extending through said base unit and said array mount to said ultrasonic transducer array and through which electrical signals are conducted to and from said ultrasonic transducer array.

8. An ultrasonic probe assembly according to claim 7 wherein said wires of said bundle of wires are coaxial cables.

9. An ultrasonic probe assembly according to claim 7 wherein said ultrasonic transducer array unit is mounted for pivotal movement over an angle of substantially one hundred and eighty degrees.

10. An ultrasonic probe assembly according to claim 9 further comprising sealing means between said ultrasonic transducer array unit and said base unit.

11. An ultrasonic probe assembly according to claim 10 wherein said base unit has an inner wall and said sealing means is attached to said ultrasonic transducer array unit and adapted to sealably contact said inner wall of said base unit.

12. An ultrasonic probe assembly according to claim 11 wherein said sealing means comprises a low friction material.

13. An ultrasonic probe assembly according to claim 5 wherein said remote control unit comprises a single bi-directional switch for controlling said first and second solenoids.

14. An ultrasonic pro,be unit according to claim 4 wherein said first and second control cables are rods.

15. An ultrasonic multi-plane probe unit for scanning a patient from within the patient's body comprising an ultrasonic probe assembly including:

(a) a base unit;

(b) an ultrasonic transducer array unit mounted to said base unit and rotatable to rotate the scan plane of a transducer array through a plurality of angular positions about a single axis, said ultrasonic transducer array unit including:
   (1) an ultrasonic transducer array for scanning in a scan plane from within a patient's body, and
   (2) a transducer mount upon which said ultrasonic transducer array is mounted,
(c) a remote control unit for selecting an angular position of said ultrasonic transducer array from outside the patient's body;
(d) drive means for rotating said ultrasonic transducer array through said plurality of angular positions about said single axis,
(e) a linearly reciprocating device, coupled to said drive means, for indexedly controlling said drive means through successive linear strokes in opposite directions in response to said remote control unit; and
means for connecting said remote control unit to signal processing and imaging equipment.

16. An ultrasonic probe according to claim 15, wherein said linearly reciprocating device includes a solenoid.

17. An ultrasonic probe according to claim 15, wherein said remote control unit includes a solenoid, and said linearly reciprocating device includes a cable or rod, coupled between said solenoid and said drive means.

18. An ultrasonic probe according to claim 17, wherein said remote control unit includes a second solenoid, and said linearly reciprocating device includes a second cable or rod, coupled between said second solenoid and said drive means.

19. An ultrasonic probe according to claim 18, wherein said drive means includes first and second linear sliding pawls, each of which is coupled to one of said cables or rods.

20. An ultrasonic probe according to claim 15, wherein said ultrasonic transducer array unit is mounted to said base unit and rotatable through a plurality of angular positions about a single axis which is normal to the plane of said ultrasonic transducer array.

* * * * *